US012415626B2

(12) United States Patent
Luker et al.

(10) Patent No.: US 12,415,626 B2
(45) Date of Patent: Sep. 16, 2025

(54) HUMAN WASTE COLLECTION SYSTEM, FOR ZERO-GRAVITY CONDITIONS, INCLUDING USER SELECTABLE MODES FOR COLLECTING LIQUID WASTE, SOLID WASTE AND MENSES

(71) Applicant: Hamilton Sundstrand Corporation, Charlotte, NC (US)

(72) Inventors: Kelly Luker, Glastonbury, CT (US); Rochelle Radawiec, Vernon, CT (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 225 days.

(21) Appl. No.: 18/366,473

(22) Filed: Aug. 7, 2023

(65) Prior Publication Data

US 2025/0051041 A1  Feb. 13, 2025

(51) Int. Cl.
  *B64G 1/60*  (2006.01)
  *A47K 11/02*  (2006.01)
  *E03D 9/08*  (2006.01)

(52) U.S. Cl.
  CPC ............... *B64G 1/60* (2013.01); *A47K 11/02* (2013.01); *E03D 9/08* (2013.01)

(58) Field of Classification Search
  CPC ............. B64G 1/60; A47K 11/02; E03D 9/08
  See application file for complete search history.

(56) References Cited

U.S. PATENT DOCUMENTS

| | | | |
|---|---|---|---|
| 3,034,131 A | 5/1962 | Paul | |
| 9,428,898 B1 | 8/2016 | Clements | |
| 9,648,996 B2 * | 5/2017 | Dreher | A47K 11/02 |
| 11,105,082 B2 | 8/2021 | Luettgen et al. | |
| 11,849,889 B2 * | 12/2023 | Qu | E03D 5/014 |
| 11,970,291 B2 * | 4/2024 | Himmelmann | A47K 11/00 |
| 2021/0017753 A1 | 1/2021 | Sylvia | |
| 2021/0062491 A1 | 3/2021 | Cao et al. | |

FOREIGN PATENT DOCUMENTS

| | | |
|---|---|---|
| JP | H01153398 A | 6/1989 |
| WO | 2020209136 A1 | 10/2020 |

OTHER PUBLICATIONS

Search Report issued in European Patent Application No. 24192962.9; Date of Mailing Jan. 9, 2025 (4 pages).

* cited by examiner

*Primary Examiner* — Janie M Loeppke
(74) *Attorney, Agent, or Firm* — CANTOR COLBURN LLP

(57) ABSTRACT

A human waste collection system having a basin defining a basin cavity and a lower end that is configured for being positioned against a floor and an upper end that is displaced further from the plane than the lower end; a storage bag system disposed in the basin cavity; a seat disposed at the upper end of the basin, the seat having a lid; a suction system having a first suction conduit extending into the basin cavity, adjacent to the upper end of the basin; a controller having a user interface that has user engageable features to select between operation modes including a first mode for removing menses and solid waste and a second mode for removing urine, wherein: in the first mode, menses and solid waste is collected in the storage bag; and in the second mode, the suction system suctions urine.

20 Claims, 3 Drawing Sheets

HUMAN WASTE COLLECTION SYSTEM, FOR ZERO-GRAVITY CONDITIONS, INCLUDING USER SELECTABLE MODES FOR COLLECTING LIQUID WASTE, SOLID WASTE AND MENSES

BACKGROUND

The embodiments herein relate to a human waste collection system, for zero-gravity conditions, including user selectable modes for collecting liquid waste, solid waste and menses.

Waste management systems in spacecraft may be uncomfortable for females to use and may require extra training to address common issues such as disposal of menses. The commercial spacecraft industry seeks for its female passengers and tourists a relatively easy to use and comfortable waste management system.

BRIEF SUMMARY

Disclosed is a human waste collection system for zero-gravity conditions, the collection system including: a basin defining a basin cavity and having a lower end that defines a lower plane and configured for being positioned against a floor and an upper end that is spaced apart from the lower end and displaced further from the plane than the lower end; a storage bag system disposed in the basin cavity; a seat disposed at the upper end of the basin, the seat including a lid pivotally coupled to the seat; a suction system including a first suction conduit extending into the basin cavity, adjacent to the upper end of the basin; a controller having a user interface that includes user engageable features to select between modes of operation including a first mode for removing menses and solid waste and a second mode for removing urine from a person seated on the seat, wherein: in the first mode, menses and solid waste is collected in the storage bag; and in the second mode, the suction system is active to apply suction to the first suction conduit for suctioning urine.

In addition to one or more aspects of the system, or as an alternate, the seat includes a flexible skirted bowl with an mesh funnel that is deployed during the second mode and is connected to the first suction conduit to urge urine toward the first suction conduit; and the flexible skirted bowl is configured to be partially or fully deployed over the basin, and connected to the first suction conduit to prevent liquid waste from flowing to the storage bag.

In addition to one or more aspects of the system, or as an alternate, the seat further includes a mesh funnel that is deployed with the flexible skirted bowl.

In addition to one or more aspects of the system, or as an alternate, the system includes an air mover that provides an air stream into the basin, adjacent to the upper end of the basin, wherein the suction system is activated when the lid is open and deactivated when the lid is closed.

In addition to one or more aspects of the system, or as an alternate, the system includes a bidet system that includes a bidet nozzle coupled to the seat, under the seat, wherein the modes of operation include a third mode for activating the bidet system; and wherein the flexible skirted bowl is configured for being deployed over the basin to block fluid flow to the basin cavity when the bidet is active.

In addition to one or more aspects of the system, or as an alternate, the seat includes a dryer that receives the air stream from the air mover, and activates during third mode to direct the airstream toward the seat, after the bidet is deactivated.

In addition to one or more aspects of the system, or as an alternate, the dryer is configured to heat the air stream.

In addition to one or more aspects of the system, or as an alternate, the system includes a UV light source within the basin, lid or seat, wherein the modes of operation include a fourth mode for sanitizing the mesh funnel, wherein in the fourth mode, the flexible skirted bowl with mesh funnel is deployed, and the UV light source is activated for a predetermined period of time.

In addition to one or more aspects of the system, or as an alternate, in the fourth mode, prior to activating the UV light source, the bidet system is activated to rinse the flexible skirted bowl with mesh funnel.

In addition to one or more aspects of the system, or as an alternate, the system includes a funnel cup that is separate from the basin and the seat; the suction system includes a second suction conduit connected to the funnel cup; and the modes of operation include a fifth mode for removal of urine from the person utilizing the funnel cup, wherein in the fifth mode, the suction system is active to apply suction to the second suction conduit.

In addition to one or more aspects of the system, or as an alternate, the system includes a pump fluidly coupled to the bidet nozzle; and a liquid supply tank fluidly coupled to the pump, for pumping bidet fluid from the liquid supply tank, through the bidet nozzle.

In addition to one or more aspects of the system, or as an alternate, the system includes the seat is removable from the basin with the bidet nozzle and the mesh funnel; and the seat includes a flexible skirted bowl that is configured for being positioned around the top of the basin.

In addition to one or more aspects of the system, or as an alternate, the system includes the flexible skirted bowl is one or more of elastic, inflatable and foldable.

In addition to one or more aspects of the system, or as an alternate, the system includes a liquid waste storage tank, wherein the suction system urges liquid waste, including urine, to the liquid waste storage tank.

In addition to one or more aspects of the system, or as an alternate, the system includes a reclamation system, wherein the suction system directs liquid waste to the reclamation system.

In addition to one or more aspects of the system, or as an alternate, the air jet system includes a fan that directs air into the dryer.

In addition to one or more aspects of the system, or as an alternate, the user engageable features include virtual or tactile buttons or voice control.

In addition to one or more aspects of the system, or as an alternate, the user engageable features are color coded to distinguish between the modes of operation.

In addition to one or more aspects of the system, or as an alternate, in one or more of the modes of operation, the system is configured to engage one or more of the bidet and the dryer for a user selectable or predetermined period of time.

Further disclosed is a lavatory for a spacecraft including: a collection system having one or more of the above disclosed features; and the suction system includes an fan that directs an air stream through the basin from the upper end of the basin to the lower end of the basin when the lid is opened.

BRIEF DESCRIPTION OF THE DRAWINGS

The present disclosure is illustrated by way of example and not limited in the accompanying figures in which like reference numerals indicate similar elements.

DETAILED DESCRIPTION

Aspects of the disclosed embodiments will now be addressed with reference to the figures. Aspects in any one figure is equally applicable to any other figure unless otherwise indicated. Aspects illustrated in the figures are for purposes of supporting the disclosure and are not in any way intended on limiting the scope of the disclosed embodiments. Any sequence of numbering in the figures is for reference purposes only.

Figure 1:
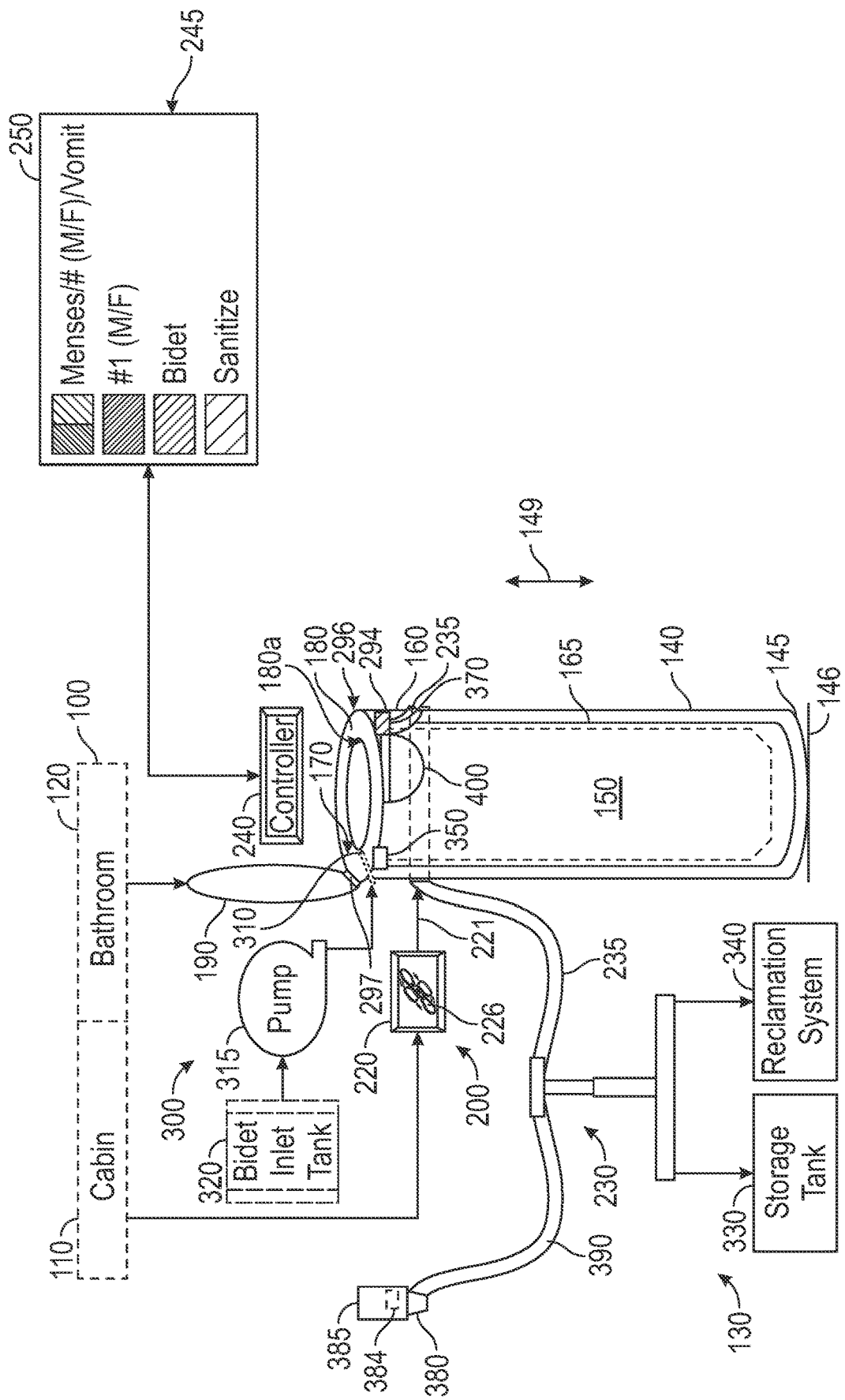
FIG. 1 shows aspects of a human waste collection system, for zero-gravity conditions, including user selectable modes for collecting liquid waste, solid waste and menses, according to an embodiment.

Turning to FIG. 1, disclosed is a spacecraft 100 including a cabin 110 and a lavatory 120 that is separate from the cabin 110. A human waste collection system (or collection system) 130 is disclosed for zero-gravity conditions.

The collection system 130 includes a basin 140 defining a basin cavity 150 and a lower end 145 that defines a lower plane 145 and is configured for being positioned against a floor (or ground) and an upper end 160 that is spaced apart from the lower end 145 and displaced further from the plane 145 than the lower end 145 (the axis 149 running from the upper end 160 to the lower end 145 defines an up-down direction for the system 130). The basin 140 may be an elongated cylindrical canister. A waste storage bag 165 is disposed in the basin cavity 150. A seat 170 is disposed at the upper end 160 of the basin 140. The seat 170 includes a base 180 and a lid 190 pivotally coupled to the seat 170 and more specifically the base 180.

The collection system 130 includes an air jet system 200. The air jet system 200 includes an dryer 350 extending into the basin 140, adjacent to the upper end 160 of the basin 140.

The air jet system 200 includes an air mover 220, which may be a fan 226, that directs an air stream 221 into the basin cavity 150, under the seat 170. More specifically, the fan 226 directs air from the cabin 110 when the lid 190 is opened (e.g., in an opened state, and is pivoted way from the seat base 180). The fan 226 may engage automatically when the lid 190 is opened and disengage when the lid 190 is closed (e.g., in a closed state, and is pivoted against the seat base 180). The air jet system 200 includes a dryer 350 that may be used in during operation of a the fan 226 and/or the bidet system 300, discussed below.

The collection system 130 includes a suction system 230. The suction system 230 includes a first suction conduit 235 extending into the basin cavity, adjacent to the upper end of the basin 140. The suction system 230 is activated by opening the lid 190 before sitting on the seat 170.

The collection system 130 includes a controller 240. The controller 240 has a user interface 245 that includes user engageable features 250 to select between modes of operation. The user engageable features 250 include virtual or tactile buttons. The user engageable features 250 may be color coded to the modes of operation disclosed herein or in a combination of such modes. The user interface 245 may also be activated by voice control.

The modes of operation include a first mode for removing menses and solid waste, and a second mode for removing urine from a person seated on the seat 170. In the first mode, the suction system 230 is activated to urge menses and any solid waste into the waste storage bag 165. The flexible skirted bowl 400 is partially deployed (FIG. 2b) but can be automatically or manually fully stowed (FIG. 2a) if the user desires. Stowed state means the entire basin 150 (and at least the entire opening 180a of the seat base 180) is clear of obstruction. In the second mode, with the bowl 400 partially deployed, the suction system 230 is active to apply suction to the first suction conduit 235 and urge urine away from a person's body, and into the storage tank 330 or reclamation system 340 with the flexible skirted bowl 400 deployed fully over the basin cavity 150.

Figure 3:
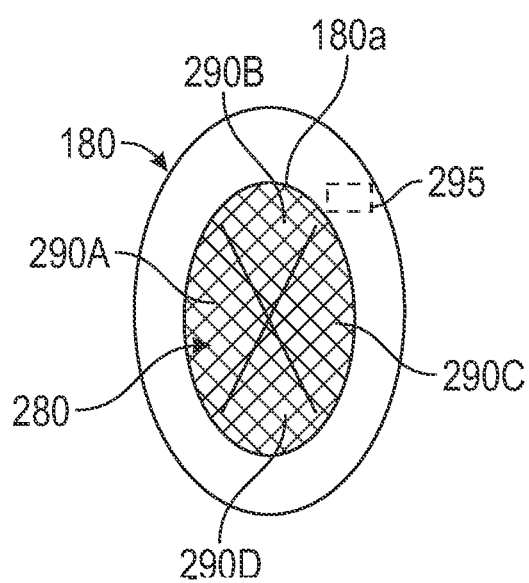
FIG. 3 shows a seat for the collection system, the seat having a base and an optional mesh funnel deployed under the base.

The flexible skirted bowl includes an internal mesh funnel 280 (FIG. 3) and is selectively deployed, e.g., by a user engageable feature such as a button on the user interface 245, e.g., via a motor 295, or automatically to a default position. This mesh funnel 280 is used to capture urine and minimize splash back on the underside of the user. The flexible skirted bowl 400 is connected to the first suction conduit 235 to pull urine into the first suction conduit 235. The mesh funnel 280 may be provided in a plurality of sections or quadrants 290A-290D. The quadrants 290A-290D may overlap to form a cohesive mesh when in use.

Figure 2A:
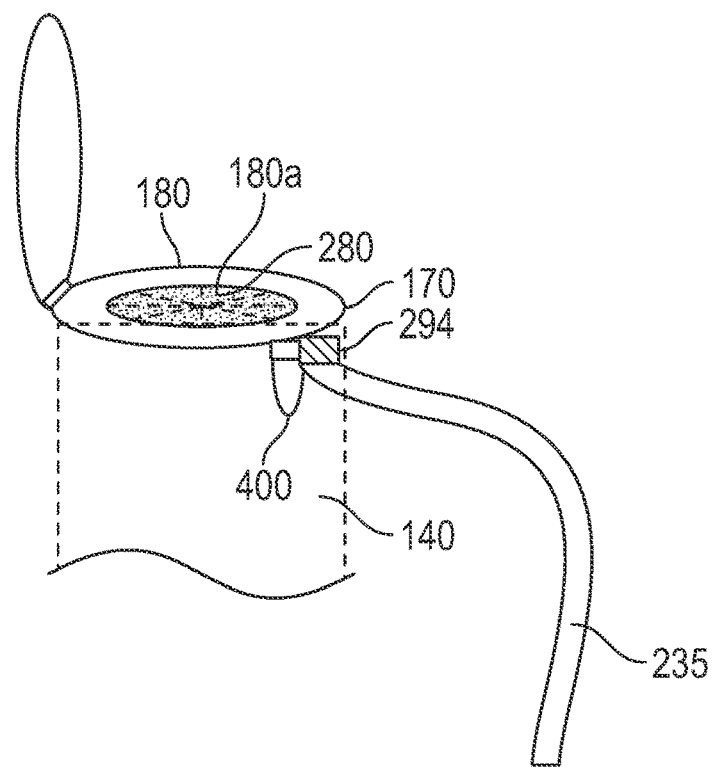
FIG. 2a shows the seat with a flexible skirted bowl in a first state, which is a fully retracted state so that it is not overlapping with a seat opening of the toilet seat.
Figure 2B:
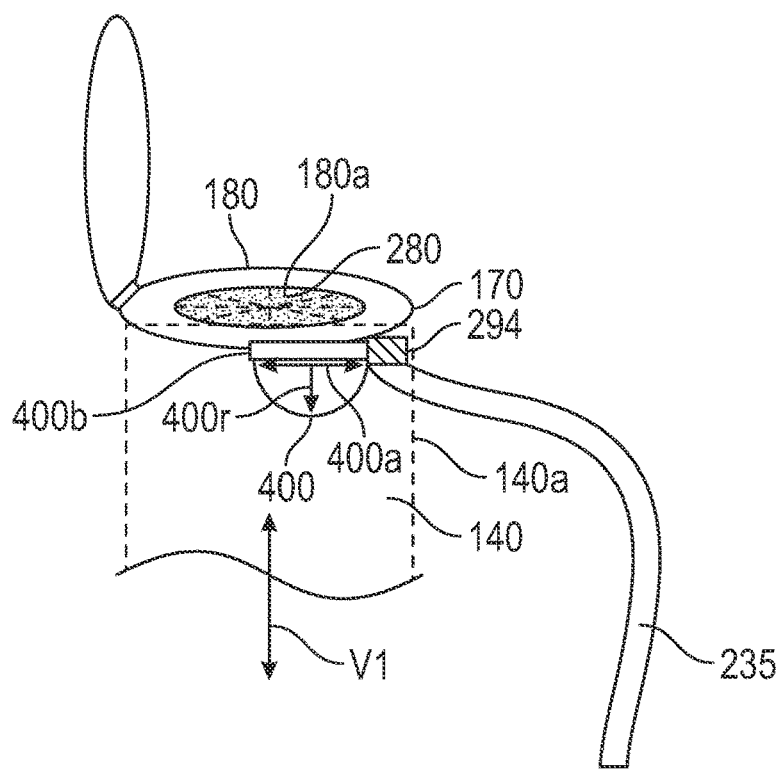
FIG. 2b shows the seat with the flexible skirted bowl in a second state, which is a partially retracted state, so that the blow extends under a forward portion of the seat opening, to form a forward catch.
Figure 2C:
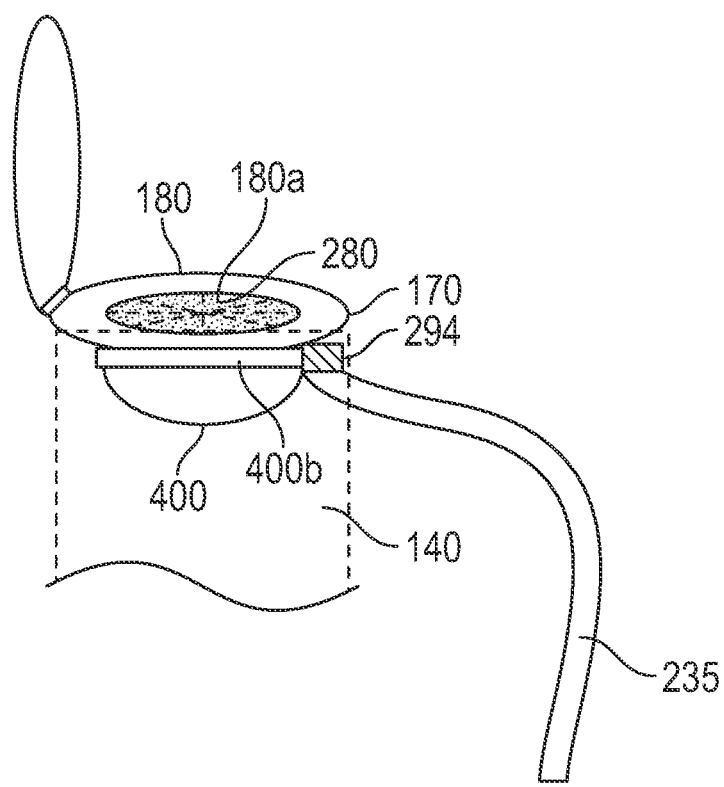
FIG. 2c shows the seat with the flexible skirted bowl in a third state, which is a fully deployed state, so that the bowl extends under substantially the entire seat opening, to form a center catch.

The seat 170 is optionally removable from the basin 140 with the bidet nozzle 310 and the mesh funnel 280. The seat 170 and more specifically the base 180 of the seat 170 includes a flexible skirted bowl 400 that is positioned fully or partially over the basin 140 and under the seat opening 180a (FIGS. 2a-2c). The flexible skirted bowl 400 may be formed of a material that is elastic, inflatable and foldable, such as an elastomer. As shown in FIG. 2b, the flexible skirted bowl 400 may have an axial portion 400a that extends axially along the basin 140, parallel to and along an underside of the seat base 180. The flexible skirted bowl 400 may have a radial portion 400R that extends radially inward along the base 180, away from the seat base 180, and may form a center catch 400, as indicated below, to prevent access to the cavity 150.

More specifically, in the second mode, the radial portion 400R of a flexible skirted bowl 400 folds out from the side, e.g., the sidewall 140a, of the basin 140 to form the center catch 400C that collects urine. Thus, urine does not go into the bag 165. The flexible skirted bowl 400 can be stowed, e.g., rolled up, or compressed, within the basin 140, against the sidewall 140a, and actuated into position, e.g., unrolled or deployed, over the bag 165 and under the seat opening 180a. The flexible skirted bowl 400 has a drain 294) fluidly coupled to the suction conduit 235 where urine is directed. The flexible skirted bowl 400 can be deployed along the horizontal axis, i.e., under and along the seat base 180, to cover the entire bag system (e.g., the entire underside of the seat opening 180a, or to be located only at the front 296 of the bag system (furthest from the seat pivot 297) during the first and second modes if desired by the user. This provides the user to opportunity to both defecate and urinate at the same time. In another embodiment, the flexible skirted bowl 400 can be moved along the vertical axis VI (toward the underside of the seat 180, along the long axis of the basin 140) for the user to seal a top flexible rim 400b of the bowl 400a it to their underside before urination. Similarly, this can move automatically or manually via hand or controller on the interface 245 or another manual controller, such as a toggle lever mounted to the basin 140 or other location. In some embodiments, positions can be programmed based on different user preferences, e.g. memory seat.

The modes of operation include a third mode (or bidet mode) for activating a bidet system 300. The bidet system 300 includes one or more bidet nozzle(s) 310 coupled to the seat 170, under the seat 170 and more specifically under the base 180. A bidet pump 315 is fluidly coupled to the bidet nozzle 310. A liquid supply tank 320 is fluidly coupled to the pump 315, for pumping bidet fluid from the liquid supply tank 320, through the bidet nozzle 310. The bidet water stream is delivered in pulses complimented by suction to prevent water accumulation. The suction system 230 may urge liquid waste, including urine and used bidet liquid, to a liquid waste storage tank 330. Alternatively, the suction system 230 may urge the liquid waste into reclamation system 340. In the bidet mode, the flexible skirted bowl 400 folds out (FIG. 2c) to the fully deployed state to over the basin cavity 150 to collect rinse water from the bidet. Thus, contaminated rinse water does not flow into the bag 165. In this mode, the flexible skirted bowl 400 will fully cover the basin cavity 150 and the seat opening 180a. The flexible skirted bowl 400 is connected to a suction conduit 235, which is attached to the front of the flexible skirted bowl 400 to not cover the basin cavity 165.

The seat 170 includes the dryer 350, as indicated. The dryer 350 activates after the bidet system 300 has completed distributing liquid from the liquid supply tank 320. The dryer 350 has an optional internal heating element, such as a coil, for a heated dry operation. In one embodiment, the rinse and dry functions may be user-operated via virtual or tactile buttons on the controller interface 245, though the use of time-based mechanisms.

The collection system 130 includes a UV light source 370 within the basin 140, lid 190, or seat 170. The modes of operation include a fourth mode for sanitizing the mesh funnel 280. In the fourth mode, the flexible skirted bowl 400 and mesh funnel 280 are fully deployed (FIG. 2c), and the UV light source 370 is activated for a predetermined period of time. In the fourth mode, prior to activating the UV light source 370, the bidet system 300 may be activated to rinse the mesh funnel 280. The UV light source 370 can also be located under the lid to sanitize the seat 170.

The collection system 130 includes a funnel cup 380 that is separate from the basin 140 and the seat 170. The suction system 230 includes a second suction conduit 390 connected to the funnel cup 380. The modes of operation include a fifth mode for removal of urine from the person utilizing the funnel cup 380. In the fifth mode, the suction system 230 is activated, e.g. by a switch associated with a funnel dock 385 in which the funnel cup 380 is stowed, to apply suction to the second suction conduit 390. The switch 384 may be a toggle switch, a pressure switch or light sensitive switch or the like that is sensitive to the removal of the funnel cup 380 from the funnel dock 385.

The embodiments herein provide a waste collection system 130 that accommodates different bodily functions for females and males by providing selectable modes of operation. The modes are selected, e.g., via user engageable features 250, which are pressed or activated by voice control to indicate which type of waste is being removed One mode of this system is directed to removing menses and solid waste. With this mode, menses and solid waste are directed into the waste storage bag 165 within a basin or canister. This mode also allows for a user to defecate and urinate at the same time via a partially deployed flexible skirted bowl 400 with a point of attachment furthest from the lid 190. A second mode is removing urine from a person sitting on the seat 170, which is typical for women and a percentage of males. In this mode, urine is suctioned away via the first suction conduit 235 or hose. A mesh funnel 280 may be deployed under the seat 170, within the flexible skirted bowl 400, which directs urine into the first suction conduit 235 and protects the fecal/menses bags. In a third mode, a bidet system 300 is utilized to enable cleaning of a person without consumable wipes and may be utilized to rinse the mesh funnel 280. The mesh funnel 280 may be reused by different persons and may be sanitized via a fourth mode (sanitation mode) of the collection system 130. In this mode, the flexible skirted bowl 400 fully covers the basin cavity 150 so that the only place liquid can be directed is into the suction conduit 235. Lastly, in a fifth mode, a funnel cup 380 may be utilized for capturing urine from a standing person.

The embodiments eliminate the need for a menses consumable filter, and consumable wipes The embodiments also provide greater female comfort by enabling a person to sit to urinate. The embodiments also provide greater user comfort by enabling a person to perform two bodily functions at once (urination and defection). The embodiments also provide a user interface 245 that is relatively easy to engage.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Those of skill in the art will appreciate that various example embodiments are shown and described herein, each having certain features in the particular embodiments, but the present disclosure is not thus limited. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

What is claimed is:
1. A human waste collection system for zero-gravity conditions, the collection system comprising:
a basin defining a basin cavity and having a lower end that defines a lower plane and configured for being positioned against a floor and an upper end that is spaced apart from the lower end and displaced further from the plane than the lower end;

a storage bag system disposed in the basin cavity;
a seat disposed at the upper end of the basin, the seat including a lid pivotally coupled to the seat;
a suction system including a first suction conduit extending into the basin cavity, adjacent to the upper end of the basin;
a controller having a user interface that includes user engageable features to select between modes of operation including a first mode for removing menses and solid waste and a second mode for removing urine from a person seated on the seat,
wherein:
  in the first mode, menses and solid waste is collected in the storage bag; and
  in the second mode, the suction system is active to apply suction to the first suction conduit for suctioning urine.

2. The collection system of claim 1, wherein:
the seat includes a flexible skirted bowl that is deployed during the second mode and is connected to the first suction conduit to urge urine toward the first suction conduit; and
the flexible skirted bowl is configured to be partially or fully deployed over the basin, and connected to the first suction conduit to prevent liquid waste from flowing to the storage bag.

3. The collection system of claim 2, wherein the seat further includes a mesh funnel that is deployed with the flexible skirted bowl.

4. The collection system of claim 3, further comprising:
an air mover that provides an air stream into the basin, adjacent to the upper end of the basin, wherein the suction system is activated when the lid is open and deactivated when the lid is closed.

5. The collection system of claim 4, further comprising:
a bidet system that includes a bidet nozzle coupled to the seat, under the seat,
wherein the modes of operation include a third mode for activating the bidet system; and
wherein the flexible skirted bowl is configured for being deployed over the basin to block fluid flow to the basin cavity when the bidet is active.

6. The collection system of claim 5, wherein:
the seat includes a dryer that receives the air stream from the air mover, and activates during third mode to direct the airstream toward the seat, after the bidet is deactivated.

7. The collection system of claim 6, wherein the dryer is configured to heat the air stream.

8. The collection system of claim 6, further comprising:
a UV light source within the basin, lid or seat,
wherein the modes of operation include a fourth mode for sanitizing the mesh funnel,
wherein in the fourth mode, the flexible skirted bowl with mesh funnel is deployed, and the UV light source is activated for a predetermined period of time.

9. The collection system of claim 8, wherein:
in the fourth mode, prior to activating the UV light source, the bidet system is activated to rinse the flexible skirted bowl with the mesh funnel.

10. The collection system of claim 9, further comprising:
a funnel cup that is separate from the basin and the seat;
the suction system includes a second suction conduit connected to the funnel cup; and
the modes of operation include a fifth mode for removal of urine from the person utilizing the funnel cup,
wherein in the fifth mode, the suction system is active to apply suction to the second suction conduit.

11. The collection system of claim 10, further comprising:
a pump fluidly coupled to the bidet nozzle; and
a liquid supply tank fluidly coupled to the pump, for pumping bidet fluid from the liquid supply tank, through the bidet nozzle.

12. The collection system of claim 11, wherein:
the seat is removable from the basin with the bidet nozzle and the mesh funnel; and
the seat includes a flexible skirted bowl that is configured for being positioned around the top of the basin.

13. The collection system of claim 12, wherein the flexible skirted bowl is one or more of elastic, inflatable and foldable.

14. The collection system of claim 12, further comprising:
a liquid waste storage tank,
wherein the suction system urges liquid waste, including urine, to the liquid waste storage tank.

15. The collection system of claim 14, further comprising:
a reclamation system,
wherein the suction system directs liquid waste to the reclamation system.

16. The collection system of claim 15, wherein:
the air jet system includes a fan that directs air into the dryer.

17. The collection system of claim 16, wherein:
the user engageable features include virtual or tactile buttons or voice control.

18. The collection system of claim 17, wherein:
the user engageable features are color coded to distinguish between the modes of operation.

19. The collection system of claim 18, wherein:
in one or more of the modes of operation, the system is configured to engage one or more of the bidet and the dryer for a user selectable or predetermined period of time.

20. A lavatory for a spacecraft, the lavatory including:
the collection system of claim 1;
the suction system includes a fan that directs an air stream through the basin from the upper end of the basin to the lower end of the basin when the lid is opened.

* * * * *